United States Patent [19]
Haber et al.

[11] Patent Number: 5,609,577
[45] Date of Patent: Mar. 11, 1997

[54] AUTOMATICALLY LOCKING HYPODERMIC NEEDLE HIDING SHIELD FOR A DOSE METERING SYRINGE

[76] Inventors: Terry M. Haber, 25011 Castlewood, El Toro, Calif. 92630; William H. Smedley, 33285 Blanche Dr., Lake Elsinore, Calif. 92330; Clark B. Foster, 23631 Wakefield Ct., Laguna Niguel, Calif. 92677

[21] Appl. No.: 593,046

[22] Filed: Jan. 29, 1996

[51] Int. Cl.[6] ..................................................... A61M 5/00
[52] U.S. Cl. ......................... 604/110; 604/192; 604/136
[58] Field of Search ...................................... 604/187, 192, 604/198, 195, 263, 218, 136, 134, 135

[56] References Cited

U.S. PATENT DOCUMENTS

| | | | |
|---|---|---|---|
| 4,787,891 | 11/1988 | Levin et al. | 604/136 |
| 5,141,496 | 8/1992 | Dalto et al. | 604/136 X |
| 5,167,632 | 12/1992 | Eid et al. | 604/195 X |
| 5,201,720 | 4/1993 | Borgia et al. | 604/198 |
| 5,364,362 | 11/1994 | Schulz | 604/198 X |

*Primary Examiner*—John D. Yasko
*Attorney, Agent, or Firm*—Morland C. Fischer

[57] ABSTRACT

A hypodermic needle shield to be coupled to a conventional dose metering syringe to hide a hypodermic needle from view of a patient (e.g. a child) to whom an injection is to be administered so as to minimize the anxiety that will be experienced by the patient. The needle shield includes an inner anchoring sleeve that surrounds and is coupled to a medication cartridge housing and an opaque needle guard that surrounds and shields the hypodermic needle that is connected in fluid communication to the medication cartridge housing. A pair of locking keys projects from the needle guard for receipt in respective guide tracks formed in the inner anchoring sleeve. The needle guard is rotated relative to the inner anchoring sleeve to cause the keys to move through the guide tracks from a first position at which the inner anchoring sleeve and medication cartridge housing are blocked from advancing distally through the needle guard to a second position at which to permit the inner anchoring sleeve and the medication cartridge housing to be advanced distally through the needle guard for unshielding the hypodermic needle during the administration of the injection.

15 Claims, 4 Drawing Sheets

AUTOMATICALLY LOCKING HYPODERMIC NEEDLE HIDING SHIELD FOR A DOSE METERING SYRINGE

BACKGROUND OF THE INVENTION

1. Field of the Invention

This invention relates to a needle shield to be coupled to a conventional dose metering syringe to hide a hypodermic needle from view of a patient to whom an injection is to be administered so as to minimize the anxiety that will be experienced by the patient prior to the injection. An additional automatic locking feature is provided that prevents the injection from being prematurely and/or accidentally administered until the needle hiding shield is first manipulated in a predetermined manner.

2. Background Art

Unique needle hiding shields to be coupled to a commercially available dose metering syringe were disclosed in our co-pending U.S. patent application Ser. No. 08/579,369 filed Dec. 27, 1995. This earlier patent application describes means by which to shield the hypodermic needle that is associated with a dose metering syringe from view of a patient (e.g. a child) so as to reduce the trauma and anxiety that will typically be experienced by the patient when the syringe is initially positioned at the targeted injection site. An injection is then administered by causing a medication cartridge housing to which the needle is connected to advance distally through the needle shield until the needle is unshielded to penetrate the patient's skin. At the conclusion of the injection, the medication cartridge housing is retracted proximally through the needle shield, whereby the needle is automatically reshielded.

It would be desirable to improve our earlier needle hiding shields by including an automatic locking feature. That is to say, the inadvertent or unintentional unshielding of the hypodermic needle prior to the injection could result in physical damage to or a contamination (i.e. loss of sterilization) of the needle. What is more, unshielding the needle after the injection has been administered could cause an accidental needle stick and the possible spread of disease. In either event, it would be advantageous to be able to lock the needle in a shielded condition and thereby prevent the accidental unshielding of the needle and the premature administration of an injection until the needle shield has first been manipulated in a precise and predetermined manner.

SUMMARY OF THE INVENTION

A needle shield is disclosed to be coupled to a conventional dose metering syringe to hide a hypodermic needle from view of a patient (e.g. a child) to whom an injection is to be administered so as to reduce the anxiety that will be experienced by the patient. A medication cartridge housing that is connected to a double ended hypodermic needle and encloses a fluid filled medication cartridge is attached to the main barrel of the dose metering syringe. A finger guard surrounds the medication cartridge housing to prevent the user of the syringe from inadvertently grasping the medication cartridge housing and impeding the distal advancement thereof. An inner anchoring sleeve is coupled to the medication cartridge housing in surrounding engagement therewith. A pair of axial spring receiving grooves having outwardly flared proximal ends are formed in the inner anchoring sleeve to establish curved paths for receiving respective coil springs that are bent along the paths. The inner anchoring sleeve also has a pair of longitudinally extending guide tracks that communicate with short circumferentially extending lock-out steps located at the distal end of the sleeve. An outer sleeve guard having a pair of keyways at the distal end thereof is fixedly connected to a cylindrical needle guard so as to surround the inner anchoring sleeve in spaced coaxial alignment therewith. The coil springs that are located within the spring receiving grooves of the inner anchoring sleeve are connected between lower spring posts at the proximal end of the outer sleeve guard and upper spring posts at the distal end of the spring receiving grooves. A sensory crown is positioned at the distal end of the needle guard. The sensory crown includes a plurality of contact points projecting therefrom to engage the targeted injection site and distract the patient's attention away from the needle strike. The needle guard and the sensory crown thereof are opaque or translucent to hide the hypodermic needle from view of the patient. A pair of keys project inwardly towards one another from the proximal end of the needle guard. In the assembled configuration, the keys of the needle guard extend through the keyways in the outer sleeve guard for receipt by respective lock-out steps formed in the inner anchoring sleeve.

With the needle shield at rest, the coil springs are in a relaxed state to urge the inner anchoring sleeve and the medication cartridge housing coupled thereto proximally of the needle guard such that the hypodermic needle that is connected to the medication cartridge housing is surrounded and shielded by the needle guard. With the keys of the needle guard received in the lock-out steps of the inner anchoring sleeve, the inner anchoring sleeve is blocked from advancing distally through the needle guard. Accordingly, the needle cannot be unshielded so as to advantageously prevent the premature or accidental administration of the injection.

To administer an injection, the contact points of the sensory crown of the needle guard are pressed against the patient's skin, and a rotational force is applied to the needle guard to cause the needle guard to rotate relative to the inner anchoring sleeve. Accordingly, the keys of the needle guard are correspondingly rotated from the lock-out steps into the longitudinally extending guide tracks of the inner anchoring sleeve. An axial pushing force is then applied to the medication cartridge housing to cause the coupled interconnection of the housing, the inner anchoring sleeve and the hypodermic needle to advance distally through the needle guard, whereby the coil springs are stretched. At the same time that the inner anchoring sleeve moves distally with the cartridge housing, the keys of the needle guard ride through the longitudinally extending guide tracks of the inner anchoring sleeve.

The distal advancement of the medication cartridge housing through the needle guard continues until the hypodermic needle is unshielded so as to penetrate the targeted injection site. The dose metering syringe is then operated in the usual fashion so that a precise volume of medication or pharmaceutical is delivered to the patient via-the hypodermic needle. When the injection has been completed, the potential energy stored by the coil springs automatically returns the needle hiding shield to the at rest condition. More particularly, the inner anchoring sleeve and the medication cartridge housing are simultaneously driven proximally relative to the needle guard so that the hypodermic needle will be withdrawn from the injection site and reshielded within the needle guard as the springs return to their original relaxed state. By virtue of the coil springs bending along a curved path formed in the inner anchoring sleeve, the keys of the needle guard will first ride through the longitudinally extending guide tracks and then automatically rotate into the lock-out steps of the inner anchoring sleeve to cause the needle guard to correspondingly rotate back to its at rest position, whereby to reestablish the locking feature of the needle hiding shield and thereby prevent the unintentional unshielding of the needle and the premature or accidental administration of an injection.

DETAILED DESCRIPTION

Figure 1:
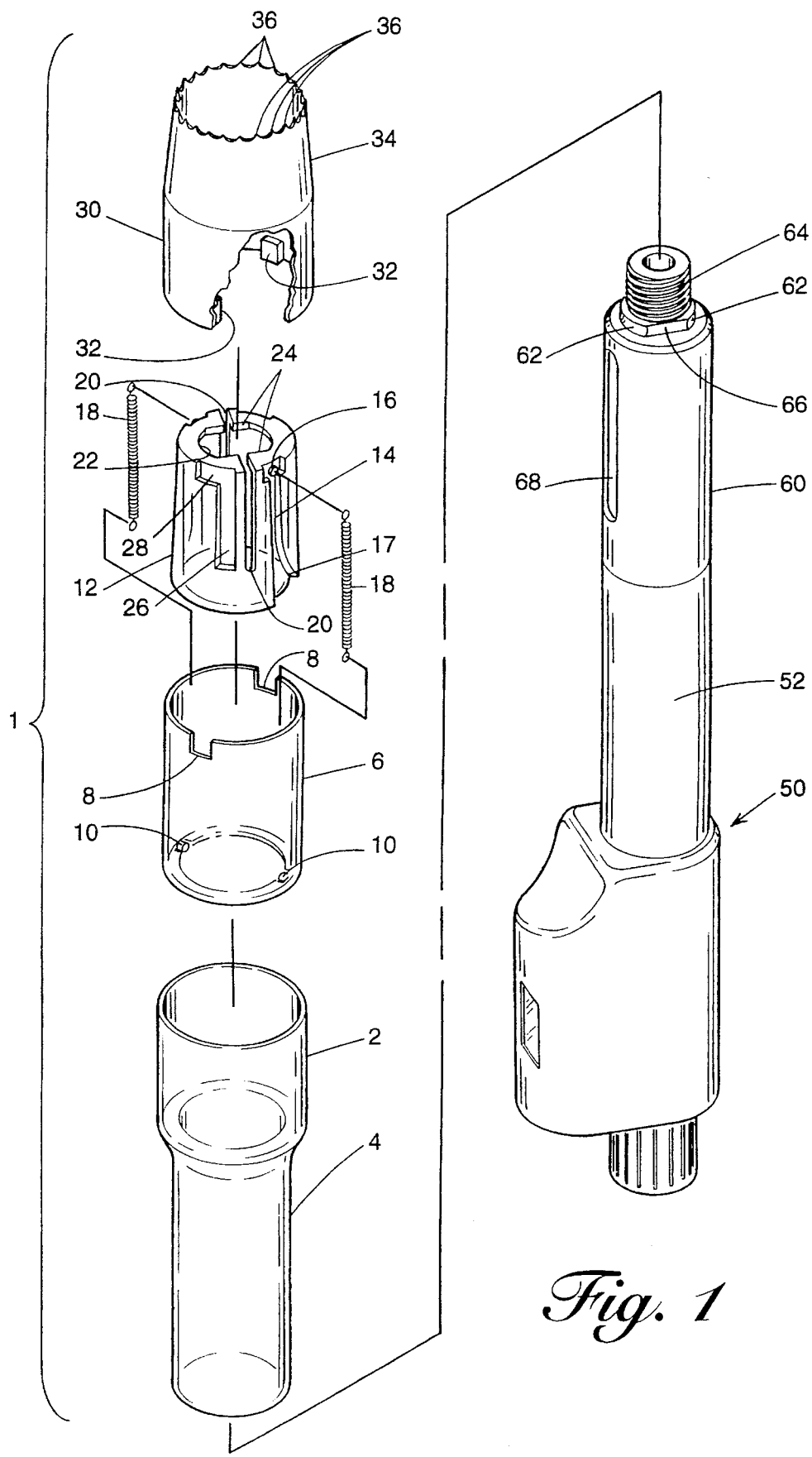
FIG. 1 is an exploded view of the automatically locking hypodermic needle hiding shield according to the present invention to be coupled to a dose metering syringe.
Figure 2:
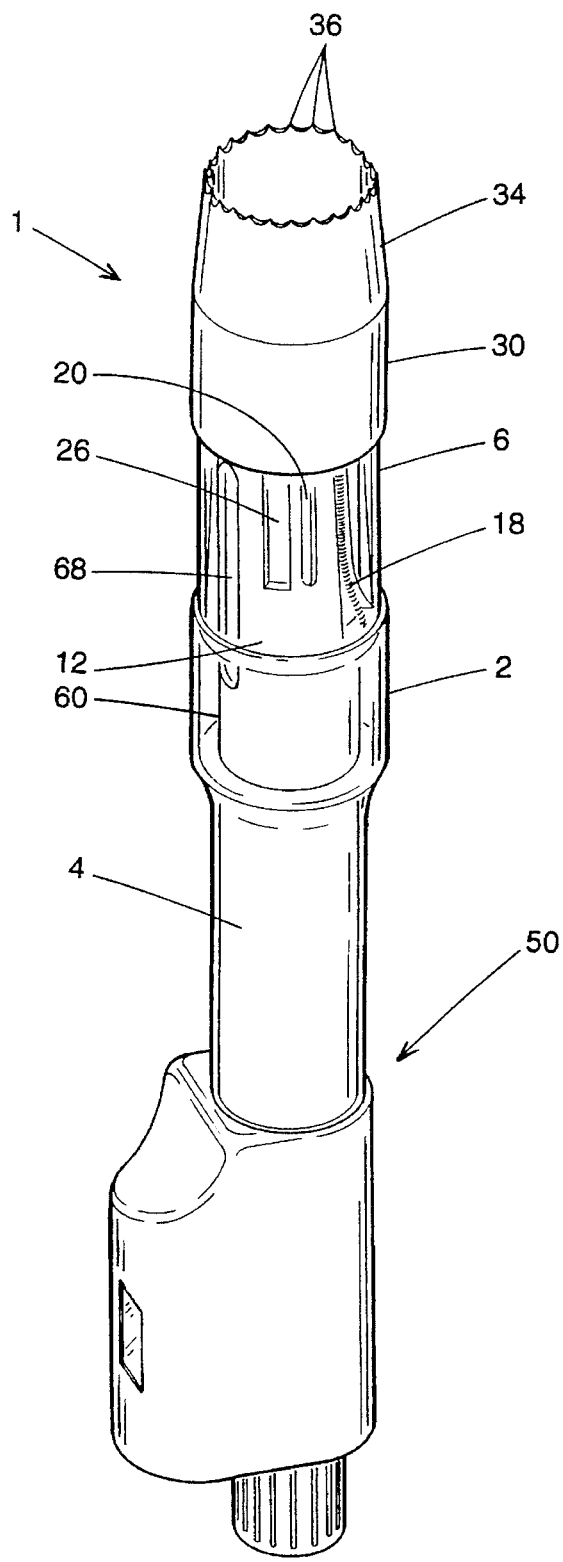
FIG. 2 shows the hypodermic needle hiding shield of FIG. 1 in the assembled relationship coupled to the dose metering syringe.

The automatically locking hypodermic needle hiding shield 1 which forms the present invention is best described while referring to the drawings, where FIGS. 1 and 2 show the needle hiding shield in exploded and assembled configurations, respectively, and adapted to be retained at the distal end of the main barrel 52 of a well known, commercially available dose metering syringe 50. Therefore, the construction and operation of dose metering syringe 50 will not be described herein. By way of example, the dose metering syringe 50 that is illustrated in the drawings is manufactured by Genentech, Inc. and sold under the trademark GenPen.

The needle hiding shield 1 includes a cylindrical finger guard 2 having a coextensive proximal sleeve 4. The proximal sleeve 4 is sized to surround and be adhesively bonded or press fit to the main barrel 52 of syringe 50 so that the finger guard 2 is retained in spaced, coaxial alignment around a soon-to-be-described medication cartridge housing 60 (best shown in FIGS. 3 and 4). The purpose of finger guard 2 is to prevent the user of dose metering syringe 50 from inadvertently grasping the cartridge housing 60 with his fingers so as to undesirably impede the travel of cartridge housing 60 relative to an outer sleeve guard 6 during the administration of an injection to a patient (e.g. a child).

The outer sleeve guard 6 is a hollow cylindrical cylinder that is preferably made from clear plastic. A pair of opposing lower spring posts 10 projects radially inward towards each other from the proximal end of the outer sleeve guard 6. The diameter of outer sleeve guard 6 is less than the diameter of the finger guard 2, so that in the assembled configuration of FIG. 2, the finger guard 2 is disposed at the proximal end of the outer sleeve guard 6 and adapted to slide axially over the outside of outer sleeve guard 6 to permit the proximal end of sleeve guard 6 to be received within finger guard 2 during the administration of the injection (also best shown in FIGS. 3 and 4).

A pair of keyways 8 are formed in the distal end of the outer sleeve guard 6. The pair of keyways 8 are oriented opposite one another and aligned so as to be ninety degrees out of phase with the pair of opposing spring posts 10 at the proximal end of sleeve guard 6. As will be explained in greater detail, the keyways 8 provide an access opening for receiving soon-to-be-described keys 32 therethrough.

Figure 3:
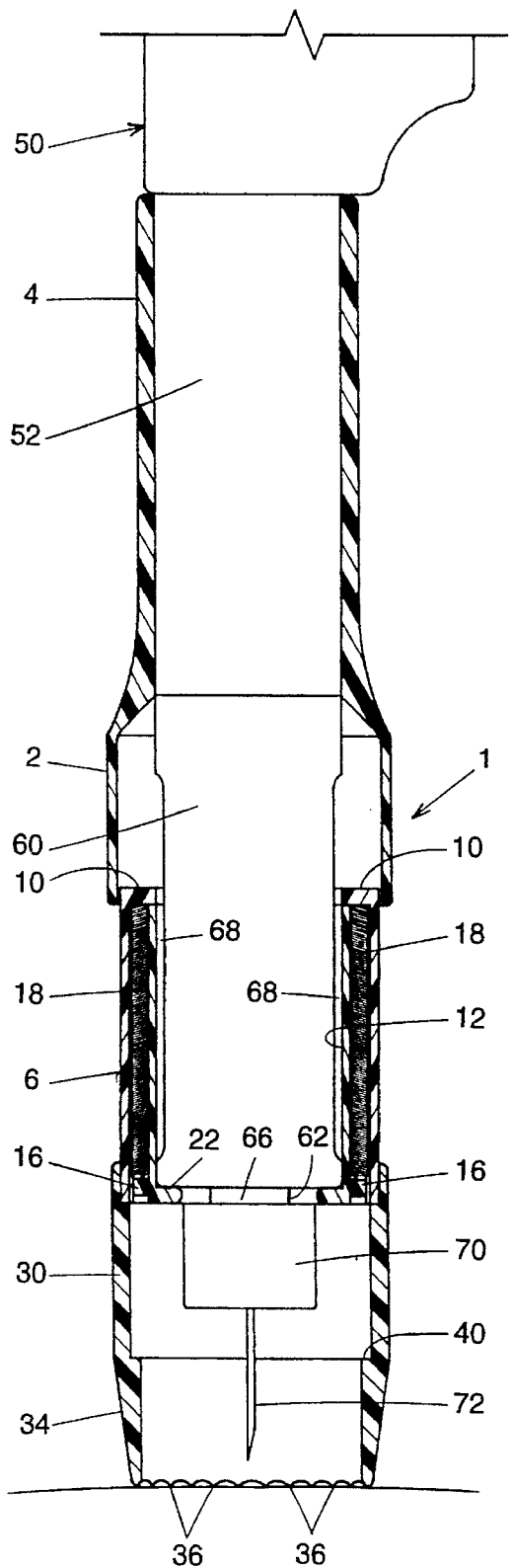
FIG. 3 shows the hypodermic needle hiding shield in an at rest condition while surrounding and shielding a hypodermic needle.
Figure 4:
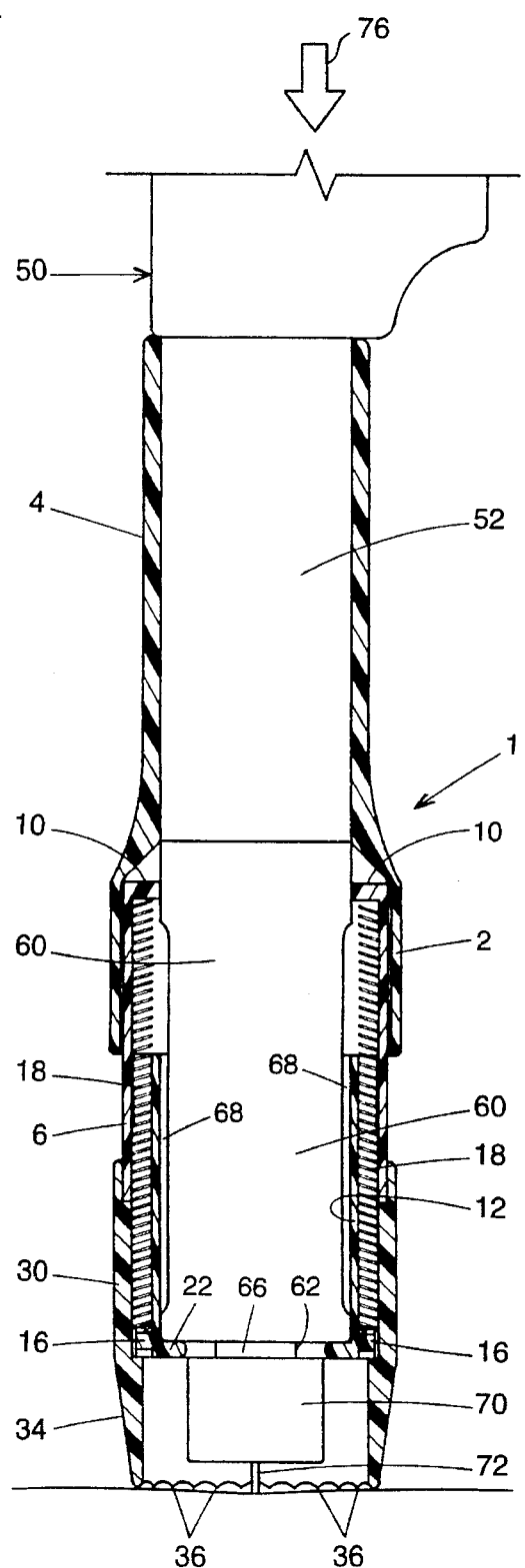
FIG. 4 shows the hypodermic needle hiding shield during the administration of an injection with the hypodermic needle unshielded and penetrating a targeted injection site.

A hollow, cylindrical inner anchoring sleeve 12 is coaxially aligned with and spaced inwardly of the outer sleeve guard 6 so that inner anchoring sleeve 12 surrounds and engages the medication cartridge housing 60 (best shown in FIGS. 3 and 4). Inner anchoring sleeve 12 has a pair of oppositely disposed, axially extending spring receiving grooves 14 (only one of which being clearly visible in FIGS. 1 and 2). A pair of upper spring posts 16 projects radially outward and away from one another at the distal ends of the spring receiving grooves 14. As an important detail of this embodiment, each of the axially extending spring receiving grooves 14 has an outwardly flared proximal end 17, the advantage of which will soon be described.

A pair of metallic, helically wound coil springs 18 are received in respective ones of the pair of spring receiving grooves 14 that are formed in the inner anchoring sleeve 12. In the assembled configuration of FIG. 2, the helically wound coil springs 18 are connected at opposite ends thereof between the lower spring posts 10 that project radially inward from the proximal end of outer sleeve guard 6 and the upper spring posts 16 that project radially outward from the distal ends of the spring receiving grooves 14 of inner anchoring sleeve 12.

Inner anchoring sleeve 12 also has a pair of longitudinally extending slots 20 that are arranged in spaced, parallel alignment with one another from the distal end of sleeve 12. The slots 20 allow the inner anchoring sleeve to dilate (i.e. flex) when exposed to an expansive force as might be encountered when sleeve 12 surrounds and engages the medication cartridge housing 60. In this regard, a circumferential collar 22 projects radially inward from the distal end of the inner anchoring sleeve 12 to be snap-fit within a pair of oppositely aligned retaining grooves 62 that are formed at the base of the usual threaded neck 64 of medication cartridge housing 60, whereby the inner anchoring sleeve 12 and the medication cartridge housing 60 are coupled to one another.

Two opposing pairs of flats 24 extend radially inward towards one another from the collar 22 of inner anchoring sleeve 12, such that each pair of flats 24 is separated by a longitudinally extending slot 20. Each pair of flats 24 is received flush against a respective alignment pad 66 that is located at the base of the threaded neck 64 of medication cartridge housing 60 between the pair of retaining grooves 62 so as to prevent a rotation of the inner anchoring sleeve 12 relative to cartridge housing 60.

As another important detail of this invention, a pair of opposing longitudinally extending guide tracks 26 (only one of which being visible in FIGS. 1 and 2) is formed in the outside of inner anchoring sleeve 12 so as to extend from the distal end thereof. Each longitudinally extending guide track 26 is coextensively joined with a short, circumferentially extending lock-out step 28 located at the distal end of the anchoring sleeve 12.

The proximal end of a hollow, cylindrical translating needle guard 30 is adhesively bonded in surrounding engagement to the distal end of the outer sleeve guard 6 so that needle guard 30 is fixedly connected to sleeve guard 6. Projecting radially inward towards one another at the proximal end of the needle guard 30 is a pair of keys 32. In the assembled relationship of FIG. 2, with needle guard 30 connected to outer sleeve guard 6, the keys 32 of needle guard 30 will project through respective keyways 8 of outer sleeve guard 6 for receipt by the guide tracks 26 or lock-out steps 28 of inner anchoring sleeve 12 for an important purpose which will be described in greater detail hereinafter.

The distal end of the needle guard 30 tapers slightly to form an integral sensory crown 34. A plurality of evenly spaced contact points (e.g. tangs) 36 project distally from the sensory crown 34. During the administration of the injection, the contact points 36 of sensory crown 34 will contact the patient's skin while surrounding the targeted injection site (best shown in FIGS. 3 and 4) so as to confuse the senses of the patient and distract the patient's attention away from the needle strike to thereby minimize patient discomfort. A peripheral travel limiting ledge 40 is located at the interface of the needle guard 30 and sensory crown 34. The needle guard 30 and sensory crown 34 are manufactured from an opaque or translucent (e.g. plastic) material so as to obscure the hypodermic needle (designated 72 in FIGS. 3 and 4) from view of the patient to whom the injection is to be administered, whereby to minimize the anxiety that will be experienced by the patient prior to the injection.

The medication cartridge housing 60 is of relatively conventional design. That is, cartridge housing 60 has a hollow cylindrical body that encloses a standard, fluid filled medication cartridge (not shown). Cartridge housing 60 includes a pair of elongated, oppositely disposed windows 68 (only one of which being visible) by which to enable the administrator of the injection to visually inspect the volume of fluid in the medication cartridge. The proximal end of the cartridge housing 60 is coupled to the main barrel 52 of the dose metering syringe 50 so that the main barrel 52 and medication cartridge housing 60 are connected end-to-end.

Medication cartridge housing 60 has a relatively narrow screw threaded neck 64 located at the distal end thereof. A corresponding screw threaded needle hub (designated 70 in FIGS. 3 and 4) that carries a double ended hypodermic needle 72 (best shown in FIGS. 3 and 4) is coupled to the cartridge housing 60 at the screw threaded neck 64 thereof, such that the proximal end of needle 72 will extend inwardly through the medication cartridge housing 60 to be placed in fluid communication with the medication cartridge that is enclosed by housing 60 (not shown), and the distal end of needle 72 will penetrate the skin of the patient to deliver the fluid contents of the medication cartridge during the injection.

However, the medication cartridge housing 60 is modified relative to conventional cartridge housings so as to include the aforementioned oppositely facing alignment pads 66 located at the base of screw threaded neck 64 between oppositely facing retaining grooves 62. As previously described, the circumferential collar 22 at the distal end of inner anchoring sleeve 12 is snap-fit within the retaining grooves 62 of medication cartridge housing 60, whereby the sleeve 12 and housing 60 are coupled to one another. As was also described, each pair of flats 24 at the distal end of inner anchoring sleeve 12 is received flush against a respective alignment pad 66 of the cartridge housing 60 to prevent the inner anchoring sleeve 12 from rotating relative to housing 60. In this regard, it may be appreciated that the alignment pads 66 are arranged ninety degrees out of phase with the windows 68 of medication cartridge housing 60 so that the springs 18 located in the spring receiving grooves 14 of the inner anchoring sleeve 12 will not block the windows 68 when the sleeve 12 and housing 60 are coupled together (as shown in FIG. 2).

The operation and automatic locking feature of the hypodermic needle hiding shield 1 of this invention is now described in detail while referring to FIGS. 3–6 of the drawings. FIG. 3 shows the needle hiding shield 1 coupled to the main barrel 52 of the dose metering syringe 50 (of FIG. 2) while the shield is at rest. More particularly, the translating needle guard 30 surrounds the targeted injection site of the patient so as to hide the hypodermic needle 72 from view of the patient to minimize patient anxiety in anticipation of the injection. In the at rest condition of FIG. 3, the needle 72 is biased in the shielded or retracted position relative to needle guard 30 in spaced alignment above the targeted injection site.

The pair of coil springs 18 connected between the lower and upper spring posts 10 and 16 are initially relaxed. Therefore, the inner anchoring sleeve 12 and the medication cartridge housing 60 to which sleeve 12 is coupled (by means of circumferential collar 22 being snap-fit within retaining grooves 62) are urged by the springs 18 so as to be disposed proximally of the needle guard 30, and the finger guard 2 that is coupled to the main barrel 52 of dose metering syringe 50 (by means of proximal sleeve 4 surrounding the main barrel 52) is positioned at the proximal end of the outer sleeve guard 6 to enclose the medication cartridge housing 60 and thereby prevent engagement of housing 60 by the fingers of the administrator of the injection.

By virtue of the present invention, the hypodermic needle 72 may not be unshielded and an injection may not be prematurely and/or accidentally administered until the administrator manipulates the needle hiding shield 1 in a predetermined manner to permit the hypodermic needle 72 to be advanced distally through the needle guard 30 towards the injection site. That is to say, the needle hiding shield 1 is initially locked in the at rest condition and the needle 72 is held in the shielded, retracted position until the needle guard 30 and the outer sleeve guard 6 connected thereto are first rotated relative to the medication cartridge housing 60 and the inner anchoring sleeve 12 coupled thereto.

Figure 5A:
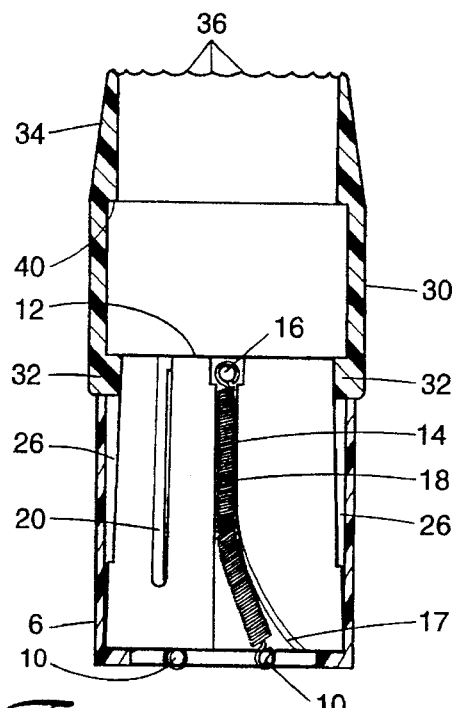
FIGS. 5A and 5B illustrate details of the hypodermic needle hiding shield in the at rest condition.
Figure 5B:
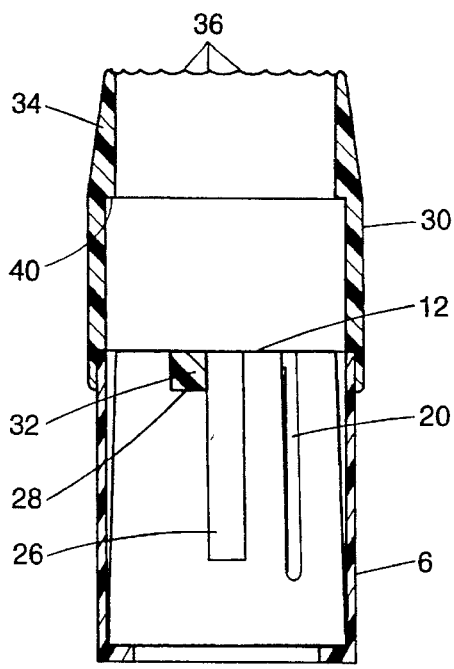

More particularly, and referring to FIGS. 5A and 5B of the drawings, the positions of the coil springs 18 in the spring receiving grooves 14 of inner anchoring sleeve 12 and the keys 32 of needle guard 30 in the lock-out steps 28 of the inner anchoring sleeve 12 are shown while the needle hiding shield 1 is at rest. It is important to note that the springs 18 in their relaxed state connected between lower and upper spring posts 10 and 16 are bent along a curved path formed by the axial spring receiving grooves 14 and the outwardly flared ends 17 thereof (best shown in FIG. 5A).

As is best shown in FIG. 5B, the keys 32 (only one of which being shown) which project inwardly of the needle guard 30 pass through the keyways 8 of outer sleeve guard 6 for receipt at the lock-out steps 28 formed in the inner anchoring sleeve 12. With the keys 32 located in respective lock-out steps 28, the inner anchoring sleeve 12 is blocked from advancing distally through the needle guard 30. What is more, the hypodermic needle 72 cannot be advanced towards the targeted injection site and unshielded, being that the medication cartridge 60 which carries needle hub 70 is coupled to the inner anchoring sleeve 12. The foregoing may be characterized as an advantageous safety feature of the present invention such that the hypodermic needle cannot be unshielded to administer the injection until the needle hiding shield 1 has first been manipulated in the manner that will now be described.

Referring now to FIGS. 5B and 5C, the hypodermic needle 72 may be unshielded when the administrator of the injection rotates the needle guard 30. With the contact points 36 of the sensory crown 34 pressed against the patient's skin, a rotational force is applied to the needle guard 30 to cause needle guard 30 and the outer sleeve guard 6 connected thereto to rotate (in the direction of the reference arrow 74) relative to the inner anchoring sleeve 12. Accordingly, the keys 32 projecting from needle guard 30 are correspondingly rotated from the lock-out steps 28 into respective longitudinally extending guide tracks 26 of inner anchoring sleeve 12.

Figure 6A:
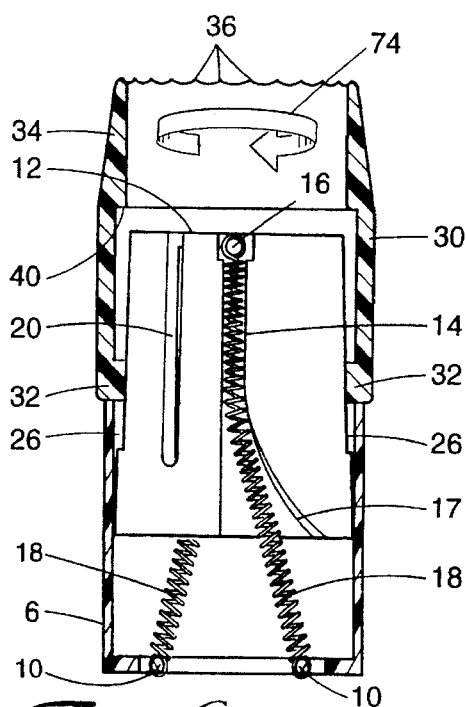
FIGS. 6A and 6B illustrate the details of the hypodermic needle hiding shield shown in FIGS. 5A and 5B during the administration of the injection.
Figure 6B:
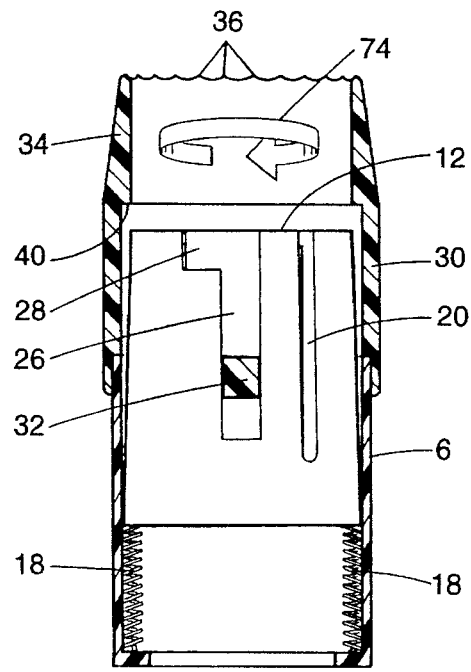

In order to administer the injection, and referring concurrently to FIGS. 4, 6A and 6B, an axial pushing force is applied (in the direction of thereference arrow 76 of FIG. 4) to the main barrel 52 of dose metering syringe 52. The axial pushing force applied to main barrel 52 is transferred to the medication cartridge housing 60 which, in turn, is advanced distally into the needle guard 30. Accordingly, the inner anchoring sleeve 12 that is coupled to the cartridge housing 60 at the retaining grooves 62 thereof moves distally through the outer sleeve guard 6, whereby to cause the pair of coil springs 18 to be stretched and thereby store potential energy (best shown in FIG. 6A). At the same time that the inner anchoring sleeve 12 moves distally with cartridge housing 60, the inwardly projecting keys 32 of the needle guard 30, which have just been rotated out of lock-out steps 28, will now ride through the longitudinally extending guide tracks 26 of sleeve 12 (best shown in FIG. 6B). Similarly, the finger guard 2 that is coupled to the main barrel 52 at proximal sleeve 4 moves distally so as to slidably receive and surround the proximal end of the outer sleeve guard 6 therewithin (best shown in FIG. 4).

The distal advancement of the medication cartridge housing 60 through the needle guard 30 continues until the hypodermic needle 72 that is coupled to cartridge housing 60 by means of needle hub 70 penetrates the targeted injection site and any further displacement of cartridge housing 60 is blocked by the travel limiting ledge 40 at the interface of the needle guard 30 and sensory crown 34 (also best shown in FIG. 4). The dose metering syringe 50 (of FIG. 2) is then operated in the usual fashion so that a precise volume of medication or pharmaceutical is delivered to the patient via hypodermic needle 72.

When the injection has been completed and the axial pushing force (represented by reference arrow 76 of FIG. 4) that has been applied to the main barrel 52 and the medication cartridge 60 is terminated, the potential energy stored by coil springs 18 automatically returns the needle hiding shield 1 to the at rest configuration of FIG. 3. That is, the inner anchoring sleeve 12 and the medication cartridge housing 60 coupled thereto are simultaneously driven proximally through the outer sleeve guard 6 so that the hypodermic needle 72 will be withdrawn from the injection site and reshielded within the needle guard 30 as the springs 18 return to their original relaxed state.

As an important advantage of the springs 18 bending along a curved path formed in the inner anchoring sleeve 12 by the axial spring receiving grooves 14 and the outwardly flared ends 17 thereof (best shown in FIG. 6A), the keys 32 of needle guard 30 will first ride through the longitudinally extending guide tracks 26 of sleeve 12 and then automatically rotate into lock-out steps 28 (as shown in FIG. 5B) to cause the needle guard 30 to rotate in a direction opposite the direction represented by reference arrow 74, whereby to reestablish the locking feature and the safety benefit of needle hiding shield 1 in the at rest condition by preventing the premature or accidental administration of an injection and thereby avoiding the possibility of an unintentional needle stick.

At the same time, the finger guard 2 is driven proximally along with cartridge housing 60 so as to slide over the outer sleeve guard 6 to return to the proximal end thereof. The dose metering syringe 50 and the needle hiding shield 1 coupled thereto may then be removed from the patient for cleaning and/or removal of the hypodermic needle 72 and medication cartridge, whereupon the process of administering the injection is completed while the patient experiences less emotional trauma as a result of not being able to see the injection taking place.

It will be apparent that while the preferred embodiment of this invention has been shown and described, various modifications and changes may be made without departing from the true spirit and scope thereof.

Having thus set forth the preferred embodiment, What is claimed is:

1. In combination:

a syringe to administer an injection, said syringe comprising a medication cartridge housing in which a fluid medication is stored and a hypodermic needle coupled to and projecting outwardly from said medication cartridge housing in fluid communication therewith; and a needle shield to shield said hypodermic needle prior to and after the administration of the injection, said needle hiding shield comprising:

an inner sleeve surrounding said medication cartridge housing and being coupled thereto, an outer sleeve surrounding said inner sleeve, a needle guard having proximal and distal ends, the proximal end of said needle guard connected to said outer sleeve, said needle guard surrounding and shielding said hypodermic needle coupled to said medication cartridge housing, spring means extending between said inner sleeve and said outer sleeve for locating said inner sleeve at the proximal end of said needle guard, said inner sleeve and said medication cartridge housing coupled thereto adapted to be advanced distally through said needle guard, and locking means releasably engaging said inner sleeve to block the distal advancement of said inner sleeve through said needle guard, said locking means releasing said inner sleeve to permit said inner sleeve and said medication cartridge housing coupled thereto to be advanced distally through said needle guard when the injection is to be administered to cause said spring means to be stretched and said hypodermic needle to be moved outwardly from the distal end of said needle guard to be unshielded and penetrate an injection site at which to deliver the fluid medication from said medication cartridge housing, said spring means relaxing at the conclusion of the injection to drive said inner sleeve and said medication cartridge housing proximally through said needle guard to retract said hypodermic needle inwardly of the distal end of said needle guard to be reshielded thereby.

2. The combination recited in claim 1, wherein said inner sleeve and said outer sleeve are arranged in spaced coaxial alignment with one another, said spring means having first and opposite ends, the first end of said spring means connected to said inner sleeve and the opposite end of said spring means connected to said outer sleeve, such that said spring means is stretched when said inner sleeve and said medication cartridge housing coupled thereto are advanced distally through said needle guard during the administration of the injection.

3. The combination recited in claim 1, wherein said needle guard is opaque to hide said hypodermic needle surrounded by said needle guard from the view of a patient to whom the injection is to be administered.

4. The combination recited in claim 1, wherein said inner sleeve has at least one spring receiving groove formed therein, said spring means received within said at least one spring receiving groove.

5. The combination recited in claim 4, wherein said at least one spring receiving groove of said inner sleeve is curved, said curved at least one spring receiving groove having a longitudinally extending first end and an outwardly flared opposite end such that said spring means is bent within said curved spring receiving groove.

6. The combination recited in claim 1, wherein said locking means includes at least one key projecting from said needle guard and a guide track formed in said inner sleeve, said at least one key being received in and riding through said guide track to block and release said inner sleeve, depending upon the location of said at least one key in said guide track.

7. The combination recited in claim 6, wherein said guide track has a first end that extends circumferentially around said inner sleeve and an opposite end that extends longitudinally along said inner sleeve, said at least one key riding between said first and opposite ends of said guide track to block said inner sleeve from being advanced distally and to release said inner sleeve to be advanced distally through said needle guard.

8. The combination recited in claim 7, wherein said needle guard is rotated relative to said inner sleeve for causing said at least one key of said needle guard to ride through said guide track between said first and opposite ends thereof to block and release said inner sleeve.

9. The combination recited in claim 1, wherein said spring means is a pair of helically wound coil springs.

10. The combination recited in claim 1, wherein said needle shield further comprising a hollow finger guard surrounding said medication cartridge housing in spaced coaxial alignment therewith to prevent manual access to said medication cartridge housing.

11. The combination recited in claim 1, wherein said inner sleeve includes a peripheral collar projecting inwardly thereof and said medication cartridge housing includes at least one retaining groove formed therein, said peripheral collar of said inner sleeve being received within said at least one peripheral groove of said medication cartridge housing whereby said inner sleeve and said medication cartridge housing are coupled to one another.

12. The combination recited in claim 11, wherein said peripheral collar of said inner sleeve includes at least one flat and said medication cartridge housing includes at least one alignment pad, said at least one flat of said inner sleeve being received flush against said at least one alignment pad of said medication cartridge housing to prevent a rotation of said inner sleeve relative to said medication cartridge housing when said inner sleeve and said medication cartridge housing are coupled together.

13. In combination:

a syringe to administer an injection, said syringe comprising a medication cartridge housing in which a fluid medication is stored and a hypodermic needle coupled to and projection outwardly from said medication cartridge housing in fluid communication therewith; and a needle shield to shield said hypodermic needle prior to and after the administration of the injection, said needle shield comprising:

an inner sleeve surrounding said medication cartridge housing and being coupled thereto, said inner sleeve having a pair of curved spring receiving grooves and a guide track formed therein, an outer sleeve surrounding said inner sleeve, a pair of springs extending between said inner sleeve and said outer sleeve, said pair of springs being received within respective ones of said pair of curved spring receiving grooves formed in said inner sleeve so that each one of said pair of springs is bent by said pair of curved spring receiving grooves, and a needle guard having proximal and distal ends and connected at said proximal end thereof to said outer sleeve, said needle guard surrounding and shielding said hypodermic needle coupled to said medication cartridge housing, said needle guard having a key projecting therefrom to be received within said guide track of said inner sleeve, said needle guard being rotated relative to said inner sleeve to cause said key to move from a first position in said guide track at which said inner sleeve and said medication cartridge housing coupled thereto are blocked from advancing distally through said needle guard to a second position in said guide track at which to permit said inner sleeve and said medication cartridge housing to be advanced distally through said needle guard when the injection is to be administered to cause said pair of springs to be stretched and said hypodermic needle to be moved outwardly from the distal end of said needle guard to be unshielded and penetrate an injection site at which to deliver the fluid medication from said medication cartridge housing, said pair of springs relaxing at the conclusion of the injection to drive said inner sleeve and said medication cartridge housing proximally through said needle guard to retract said hypodermic needle inwardly of the distal end of said needle guard to be reshielded thereby.

14. The combination recited in claim 13, wherein said needle guard is opaque to hide said hypodermic needle surrounded by said needle guard from view of a patient to whom the injection is to be administered.

15. The combination recited in claim 13, wherein said guide track has a first end that extends circumferentially around said inner sleeve and an opposite end that extends longitudinally along said inner sleeve, said key projecting from said needle guard riding from said first position located at said first end of said guide track to said second position located at said opposite end of said guide track to block said inner sleeve from being advanced distally and to release said inner sleeve to be advanced distally through said needle guard.

* * * * *